United States Patent
Sjostedt

(10) Patent No.: US 8,092,260 B2
(45) Date of Patent: Jan. 10, 2012

(54) DEVICE FOR SECURING LEADS INTO IN-LINE CONNECTOR DEVICES

(75) Inventor: Rob Sjostedt, Foothill Ranch, CA (US)

(73) Assignee: Bal Seal Engineering, Inc., Foothill Ranch, CA (US)

( * ) Notice: Subject to any disclaimer, the term of this patent is extended or adjusted under 35 U.S.C. 154(b) by 186 days.

(21) Appl. No.: 12/510,069

(22) Filed: Jul. 27, 2009

(65) Prior Publication Data

US 2010/0029127 A1 Feb. 4, 2010

Related U.S. Application Data

(60) Provisional application No. 61/085,276, filed on Jul. 31, 2008.

(51) Int. Cl.
*H01R 24/04* (2006.01)

(52) U.S. Cl. ........................................ 439/669; 439/587

(58) Field of Classification Search ................ 439/274, 439/275, 454, 462, 587, 669; 174/152 R
See application file for complete search history.

(56) References Cited

U.S. PATENT DOCUMENTS

| | | | | | |
|---|---|---|---|---|---|
| 1,882,856 | A | * | 10/1932 | Meuer | 439/462 |
| 2,305,150 | A | * | 12/1942 | Fearon | 174/167 |
| 3,046,515 | A | * | 7/1962 | Appleton | 439/186 |
| 3,668,612 | A | * | 6/1972 | Nepovim | 439/584 |
| 3,854,789 | A | * | 12/1974 | Kaplan | 439/584 |
| 6,045,403 | A | * | 4/2000 | Werner et al. | 439/587 |
| 6,190,180 | B1 | | 2/2001 | Purington | |
| 6,454,602 | B1 | * | 9/2002 | Sharrow | 439/584 |
| 2005/0215943 | A1 | | 9/2005 | Brandenburger et al. | |
| 2008/0135586 | A1 | | 6/2008 | Pardes et al. | |

OTHER PUBLICATIONS

International Search Report completed Mar. 15, 2010 and mailed Mar. 17, 2010 from corresponding International Application No. PCT/US2009/051930, filed Jul. 28, 2009 (4 pages).
Written Opinion completed Mar. 15, 2010 and mailed Mar. 17, 2010 from corresponding International Application No. PCT/US2009/051930, filed Jul. 28, 2009 (5 pages).

* cited by examiner

*Primary Examiner* — Thanh Tam Le
(74) *Attorney, Agent, or Firm* — Klein, O'Neill & Singh, LLP

(57) ABSTRACT

A locking device for connectors is provided that uses a threaded seal latch application using a ferrule. The locking device secures leads in electrical connectors, particularly connectors involved in medically implantable devices. The locking device utilizes a threaded nut, pre-assembled onto a lead cable with a ferrule. The lead cable is inserted into and engages with a threaded sleeve, the threaded sleeve serves as an opening for the in-line stack inside a housing. The threaded nut engages the threaded sleeve, and the ferrule along the lead cable is encased therebetween. The ferrule is pushed into and against the inner surface of the threaded sleeve by the threaded nut, tightly securing the ferrule in place, and thereby locking the lead cable in the desired position.

16 Claims, 4 Drawing Sheets

DEVICE FOR SECURING LEADS INTO IN-LINE CONNECTOR DEVICES

CROSS-REFERENCE TO RELATED APPLICATION

This is a regular utility application of Provisional Application No. 61/085,276, filed Jul. 31, 2008, the contents of which are expressly incorporated herein by reference.

BACKGROUND

The present invention relates generally to locking devices for connectors, and particularly to a means of securing an implantable lead in a stack of electrical connectors, particularly for an implantable medical device, with a threaded seal latch using a ferrule or molded bead feature, collectively or individually otherwise referred to as an enlarged member or section located on a lead.

Generally, connecting a lead to an implantable medical device involves the use of an additional set screw to restrain the lead, if not to facilitate the connection altogether. To achieve connecting and locking of the lead, the prior art typically involves the use of a set screw that is screwed into an additional hole threaded radially to an axis of insertion within the implantable device header that holds the lead in the medical device. The inserted set screw radially engages the side of the lead, applying a force or mechanical interference between the end of the screw and the lead, thereby securing the position of the lead within the medical device.

However, in these devices, after only a few insertions and removals of the set screw, metal shavings from the threaded portions can enter the lead cavity or spread out into the human body, leading to contamination and possibly complications. In addition, once the set screw is inserted into these devices, there is no opportunity for visual inspection, and there is no way to ensure that the connection is secure. Furthermore, the set screw hole is an additional potential leakage source for body fluids to enter the medical device. The set screw assembly must be sealed with silicone filler once the screw is inserted to prevent leakage, and removal of the set screw requires removal of the filler. Additionally, the set screw can become accidentally disconnected from the device during surgery and can be lost in the body. Finally, the set screw requires a tool to operate and thereby increases the complexity of the device or at least requires additional steps during surgery.

Connectors having multiple in-line contacts, such as audio plugs, can also benefit from improved securing means.

SUMMARY

Aspects of the present invention may be practiced by providing a locking and sealing mechanism for a medically implantable device. The mechanism may comprise a sleeve on the medically implantable device, the sleeve including a first threaded member extending externally of the medically implantable device, and an opening running longitudinally from an end of the first threaded member into the medically implantable device; a lead sized for insertion into the opening, the lead including a ferrule component or molded bead with a diameter greater than the diameter of the opening, and a second threaded member positioned proximally to the ferrule component or molded bead, the second member moveable along the axis of the lead with an opening smaller than the diameter of the ferrule component or molded bead. The second threaded member is configured to engage with the first threaded member, thereby preventing removal of the lead from the opening; wherein the locking mechanism also seals the opening from the outside environment.

In a further aspect of the present invention, a locking mechanism for a medically implantable device is provided comprising a sleeve on the medically implantable device, the sleeve including a first threaded member extending externally of the medically implantable device, and an opening to a cavity at an end of the externally extending first threaded member, said cavity tapering inwardly from said opening to form an entrance to a bore. The mechanism further includes a lead sized for insertion into the opening and the bore of the sleeve, the lead having a nominal outside diameter section and including an enlarged section with an outer diameter greater than the nominal outside diameter section of the lead and a second threaded member for surrounding the enlarged section, the second threaded member being moveable along the axis of the lead. In particular aspects of the present invention, the second threaded member is threadedly engaged to the first threaded member to secure, at least in part, the enlarged section within the cavity of the sleeve and to secure the lead, at least in part, within the bore of the sleeve.

In another aspect of the present invention, there is provided a method for locking a lead to an implantable medical device. The method comprising inserting the lead into a common bore of a header stack and a bore of a sleeve comprising an elongated section comprising exterior threads. Positioning a ferrule into mechanical communication with the sleeve and the lead, and turning a nut comprising interior threads to engage the exterior threads of the elongated section.

In another aspect of the present invention, there is provided an implantable medical device comprising an in-line connector stack having a common bore attached to a header and the header is attached to a sealed implantable housing. A locking device having a portion covered by the header and a portion extending away from the header is incorporated, said locking device comprising a threaded nut and a sleeve comprising a bore aligned to the common bore of the in-line connector stack and having a removable ferrule received in a bore holding section, wherein the ferrule is configured to compress inside the bore holding section when the threaded nut is threaded to the sleeve.

In a yet further aspect of the present invention, there is provided a locking device for use with an implantable medical stack, said locking device comprising a body comprising two spaced apart flanges defining a secured space therebetween; a bore extending through the body, a cylindrical section comprising external threads extending axially away from one of the two flanges: a ferrule received in a section of the bore, said ferrule comprising a frustoconical shaped body comprising a first open end and a second open end; and a nut threadedly attached to the cylindrical section.

Either the ferrule component or a molded bead, otherwise known as an enlarged section or member positioned on the lead, along with the first and second threaded members can accomplish the locking restraint of the lead and the necessary sealing of the lead to the medical device.

As an additional example, a locking mechanism for a connector comprising a sleeve located on a housing having a first threaded member extending externally of the housing and having an opening to a cavity at an end of the externally extending first threaded member is provided. The cavity tapering inwardly from said opening to form an entrance to a bore. A lead sized for insertion into the opening and the bore of the sleeve is provided. The lead having a nominal outside diameter section and including an enlarged section with an outer diameter greater than the nominal outside diameter section of the lead. A second threaded member for surrounding the enlarged section is also provided, the second threaded member being moveable along the axis of the lead. In a particular embodiment, the second threaded member is threadedly engaged to the first threaded member to secure, at least in part, the enlarged section within the cavity of the sleeve and to secure the lead, at least in part, within the bore of the sleeve.

Another aspect of the present invention include an in-line connector comprising an in-line stack having a common bore positioned in a housing, which is attached to source generator or a source receiver, such as a radio and an outlet. A locking device comprising a portion covered by the housing and a portion extending away from the housing is provided, said locking device further comprising a threaded nut and a sleeve comprising a bore aligned to the common bore of the in-line stack and having a removable ferrule received in a bore holding section of the sleeve. In a particular embodiment, the ferrule is configured to compress inside the bore holding section when the threaded nut is threaded to the sleeve.

A still further aspect of the present invention include a locking device for use with an in-line connector. In particular embodiments, the locking device comprises a body comprising two spaced apart flanges defining a space therebetween, a bore extends through the body; and a cylindrical section comprising external threads extending axially away from one of the two flanges. The device further includes a ferrule received in a section of the bore, said ferrule comprising a frustoconical shaped body comprising a first open end and a second open end and a nut threadedly attached to the cylindrical section.

Features of the present invention also include methods for making and/or using a locking device for use with an-line connector stack. In one embodiment, a method for locking a lead to an in-line stack is provided that comprises inserting the lead into a common bore of the in-line stack and a bore of a sleeve comprising an elongated section comprising exterior threads. The method further comprises the step of positioning a ferrule in mechanical communication with the sleeve and the lead, and turning a nut comprising interior threads to engage the exterior threads of the elongated section.

DETAILED DESCRIPTION

The detailed description set forth below in connection with the appended drawings is intended as a description of the presently preferred embodiments of a locking device for connectors provided in accordance with aspects of the present invention and is not intended to represent the only forms in which the present invention may be constructed or utilized. The description sets forth features and steps for constructing and using the locking device of the present invention in connection with the illustrated embodiments. It is to be understood that the same or equivalent functions and structures may be accomplished by different embodiments that are also intended to be encompassed within the spirit and the scope of the invention. As denoted elsewhere herein, like element numbers are intended to indicate like or similar elements or features.

Figure 1:
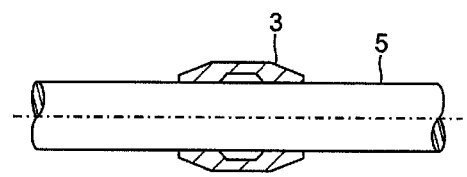
FIG. 1 shows a cross section of a ferrule assembled onto a portion of an implantable lead.

FIG. 1 shows a cross section of a ferrule assembled onto a portion of the implantable lead.

Figure 2A:
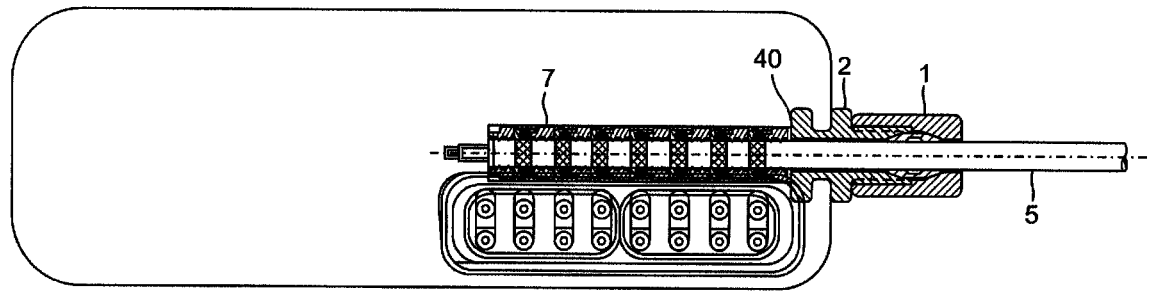
FIG. 2a is a top view and FIG. 2b is a side view of a medical device with a lead assembled into a connector of the medical device in accordance with aspects of the invention.
Figure 2B:
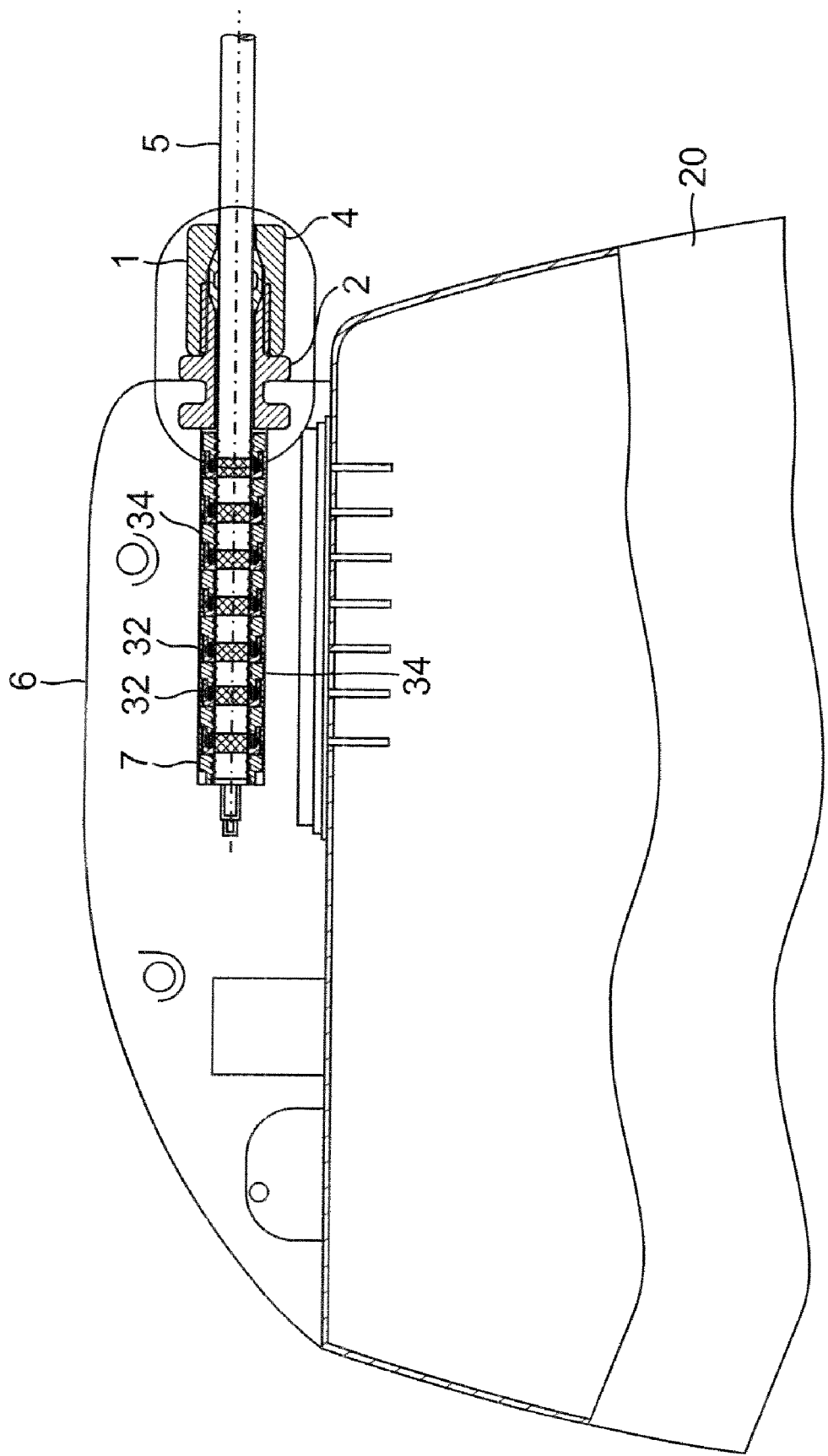

FIG. 2a shows a top view and FIG. 2b shows a side view of an implantable lead 5 inserted into a connector or stack 7 located in a header 6, for example, an implantable pulse generator header, of an implantable medical device 20, and locked in position by a locking device 1, in accordance with aspects of the invention. Exemplary connectors or stacks are disclosed in Ser. No. 61/044,408, filed Apr. 11, 2008, entitled Encapsulated Connector Stack: Ser. No. 12/102,626, filed Apr. 14, 2008, entitled Electrical Connectors with Improved Electrical Contact Performance, and Ser. No. 12/062,895, filed Apr. 4, 2008, entitled Connector Assembly for Use with Medical Devices. The contents of each of the applications are expressly incorporated herein by reference as if set forth in full. The '895 application discloses. among other things, an implantable lead comprising conductive elements and non-conductive elements spaced along at least a section of the lead. The conductive elements are configured to contact the springs in the in-line connector stack of the disclosed implantable medical device. The connector or stack comprises at least two conductive rings 32 each comprising a bore spaced apart from one another by a non-conductive spacer 34, which in the embodiment shown is a non-conductive seal element. The at least two conductive rings are each equipped with an electrode that is in turn connected to an electronic or electrical source. such as to a power terminal or a circuit board.

The locking device 1 may be a threaded seal latch and may include a threaded nut 4, or similar threaded member, assembled or mounted onto the implantable lead 5. The threaded nut 4 is configured to engage a threaded sleeve 2, or similar complimentary threaded member, which may be part of the header 6 of the medical device 20, such as by co-molding or pre-molding the part of the sleeve along with the stack with the header. In one embodiment, the threaded sleeve 2 is placed adjacent the open end of the connector or stack 7 and the two are over-molded to the sealed implantable device housing. In other embodiments, the sleeve 2 has a far end 40 (FIG. 2a) having an annular ring for placing around an exterior surface of an end of the stack 7 to facilitate aligning the sleeve 2 to the stack before molding. Other variations for aligning the two are contemplated and are considered within the purview of the present invention, such as using a boss and a pin or companion shoulders.

The threaded sleeve 2 is configured to engage with or to a ferrule 3 to prevent leakage around the lead 5. A locking device using a combination ferrule and threaded nut has several advantages over a set screw assembly of the prior art, for example and among other things, improved sealing properties, allowing a clear view of the distance the threaded nut has been screwed onto the threaded sleeve, and eliminating over-molding or application of any additional filler material, such as around the opening for the set screw. Additionally, the locking device may be engaged without the use of special tools.

In one embodiment, the threaded sleeve 2 is a singularly formed body comprising two spaced apart flanges 8, 9 defining a gap therebetween for receiving over-mold material, A cylindrical projection 10 having exterior threads 10a (FIG. 3a) axially projects from the second flange 9 for threaded engagement with the threaded nut 4. A frustoconical cavity 42 for receiving the ferrule 3 is located at the axial end of the cylindrical projection 10. The nut 4 has a similar frustoconical end 44 for receiving the opposite end of the ferrule. In one embodiment, the locking device 1 is made from a medical grade implantable metal, However, the ferrule may be made from a hard implantable thermoplastic material, for example PEEK, or molded as a bead on the silicone jacketed lead. Thus, the present header incorporates a sleeve having an opening leading to a cavity that is sized to receive a ferrule. However, the cavity tapers inwardly towards a central axis to a nominal inside diameter of a bore, which is sized to receive the medical lead 5. The nominal inside diameter is approximately the same size as the inside diameter of the stack 7, which is also sized to receive the medical lead as explained in the three applications incorporated hereinabove.

Figure 3A:
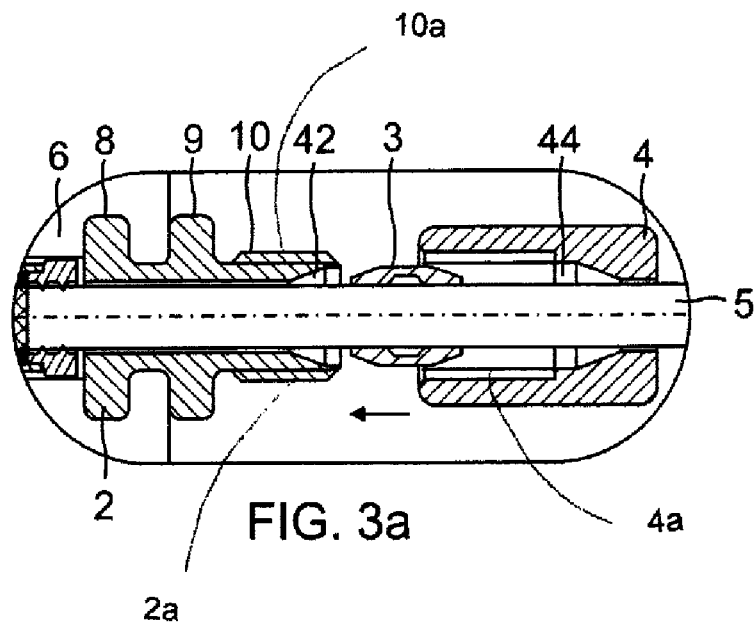
FIGS. 3a, 3b, and 3c show a sequence in which an implantable lead is assembled and locked by an engagement of the locking device in accordance with aspects of the invention

FIG. 3a shows a locking device in a disassembled position or state. The locking device includes a threaded sleeve 2 comprising a first threaded member 2a fixed in a header 6 of a medical device, and a threaded nut 4 comprising a second threaded member 4a. The threaded sleeve 2 engages the ferrule 3 along an inner surface of the exposed side edge of the threaded sleeve 2. The threaded nut 4 may be pre-assembled onto an implantable lead 5 (labeled in FIG. 3c) subsequent to the ferrule 3 on the implantable lead 5. The threaded nut 4 and threaded sleeve 2 both generally consist of inner diameters less than the maximum diameter of the ferrule 3, In FIG. 3a, the implantable lead 5 is shown partially inserted into threaded sleeve 2 and the ferrule 3 is positioned between the threaded sleeve 2 and threaded nut 4.

FIG. 3a shows a locking device in a disassembled position or state. The locking device includes a threaded sleeve 2 fixed in a header 6 of a medical device, and a threaded nut 4. The threaded sleeve 2 engages the ferrule 3 along an inner surface of the exposed side edge of the threaded sleeve 2. The threaded nut 4 may be pre-assembled onto an implantable lead 5 (labeled in FIG. 3c) subsequent to the ferrule 3 on the implantable lead 5. The threaded nut 4 and threaded sleeve 2 both generally consist of inner diameters less than the maximum diameter of the ferrule 3. In FIG. 3a, the implantable lead 5 is shown partially inserted into threaded sleeve 2 and the ferrule 3 is positioned between the threaded sleeve 2 and threaded nut 4.

In one embodiment, the ferrule 3 comprises of a section with a larger inner diameter than that at the axial openings, resembling an enlarged cavity 46. Its overall configuration resembles a double ended frustoconcial element. When the locking device is assembled, the relative dimensions of the locking device and the ferrule causes the axial ends of the ferrule to compress against the exterior surface of the lead to seal against the lead. Thus, aspects of the present invention is an implantable medical connector comprising a plurality of alternating conductive cylindrical members and non-conductive cylindrical members and a sleeve molded into a header, said sleeve comprising a section extending outwardly from the header and providing an opening; wherein said opening forms part of a frustoconical section for receiving an enlarged member or section for forming a seal with an implantable medical lead. In an exemplary embodiment, the enlarged member comprises a ferrule slidably movable relative to the medical lead. In other embodiments, the ferrule forms a fluid tight seal against the exterior surface of the medical lead when the ferrule is axially compressed by the sleeve and a threaded nut. In yet another embodiment, as further discussed below, the enlarged member is a bead formed upon the lead.

Figure 3B:
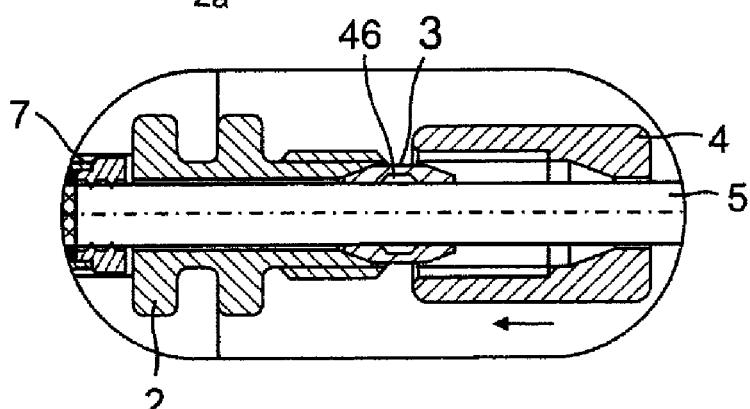

FIG. 3b shows the locking device 1 in a partially locked position. The implantable lead 5 is fully inserted into the threaded sleeve 2 and the ferrule 3 is engaged to the threaded sleeve 2. Once inserted, electrical terminals on the lead cable 5 make electrical contacts with corresponding contact springs on the connector 7, as described in the three applications previously incorporated herein by reference. In FIG. 3b, the threaded nut 4 is not yet engaged with the threaded sleeve 2.

Figure 3C:
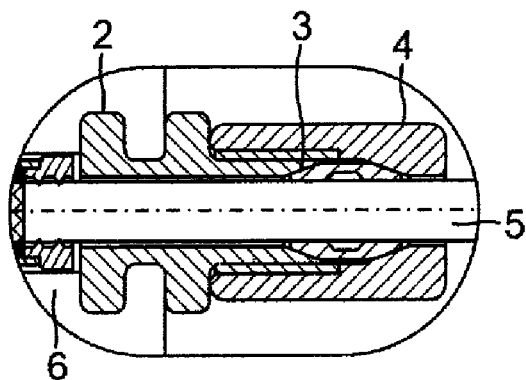

FIG. 3c shows the locking device in an assembled position. The ferrule 3 is engaged with threaded sleeve 2 and the threaded nut 4, and threaded nut 4 is fully engaged with the threaded sleeve 2. When in the assembled position, the threaded sleeve 2 and the threaded nut 4 restrict movement of ferrule 3, thus locking the position of the implantable lead 5 in the threaded sleeve 2, and thereby also locking the implantable lead 5 in position in the header 6 of the medical device. Once the locking device is assembled, a liquid tight seal is formed between the ferrule and the exterior circumference of the lead cable and between the ferrule and the cylindrical section 10 of the sleeve 2, at the frustoconical cavity. The ferrule seals against the implantable lead 5 when the sleeve and the threaded nut axially compress the ferrule and causing the ferrule to radially compress against the exterior surface of the lead.

Aspects of the invention, therefore, are directed toward a locking device which locks an implantable lead inserted into an implantable medical device. In some embodiments of the invention, the locking device is external to the medical device in both disassembled and assembled positions, allowing for more accurate testing and inspection of the locking mechanism and providing confidence of proper assembly to users of the locking device. In another example, an in-line connector comprising at least two conductive rings spaced apart from one another by a non-conductive spacer in a housing is provided for receiving a lead cable, which has at least two corresponding conductive contacts spaced from one another to electrically communicate with the at least two conductive rings, and wherein a sleeve and a nut are provided comprising a cavity for receiving a sealing section having a frustoconical end on the lead cable for sealingly securing the lead cable to the housing. In one specific example, the sealing section on the lead cable is a slidable ferrule having two frustonical ends. In another example, the sealing section on the lead cable is a bead fixedly secured to the lead cable. It is further understood that at least two conductive rings located in the housing and the at least two conductive contacts on the lead cable are connected to a source generator and a source receiver, such as a radio and an electrical source, as a simple example.

Figure 4:
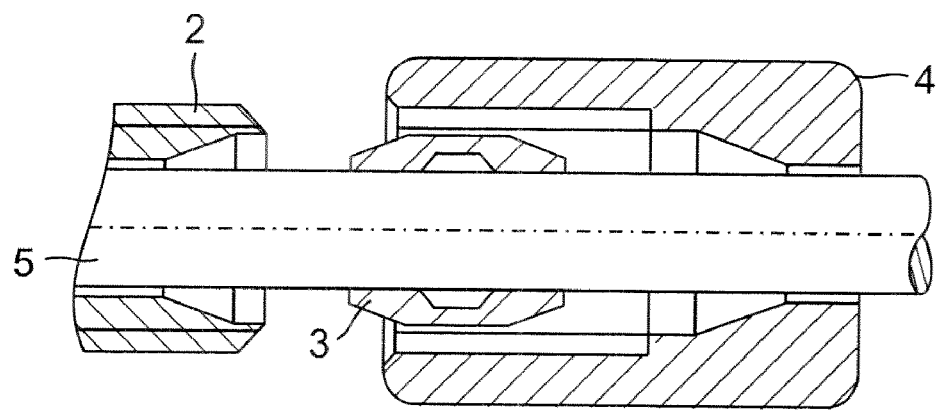
FIG. 4 is an enlarged sectional view of FIG. 3a with the ferrule further positioned inside the cavity of the nut.

FIG. 4 is an enlarged cross-sectional side view of the locking device of FIG. 3a with the ferrule positioned further into the cavity of the threaded nut.

Figure 5:
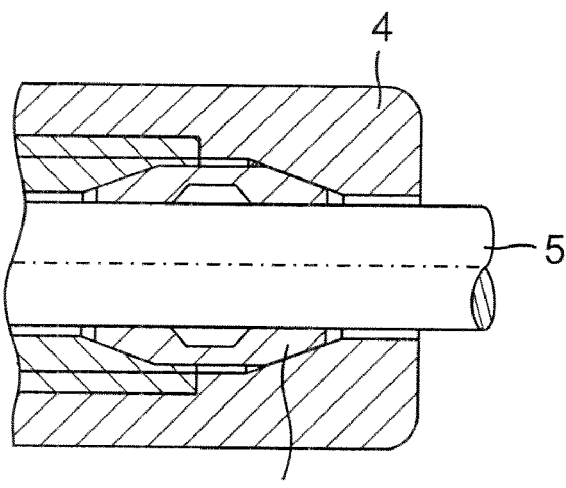
FIG. 5 is an enlarged sectional view of FIG. 3c.

FIG. 5 is an enlarged cross-sectional side view of the locking device of FIG. 3c.

Figure 6:
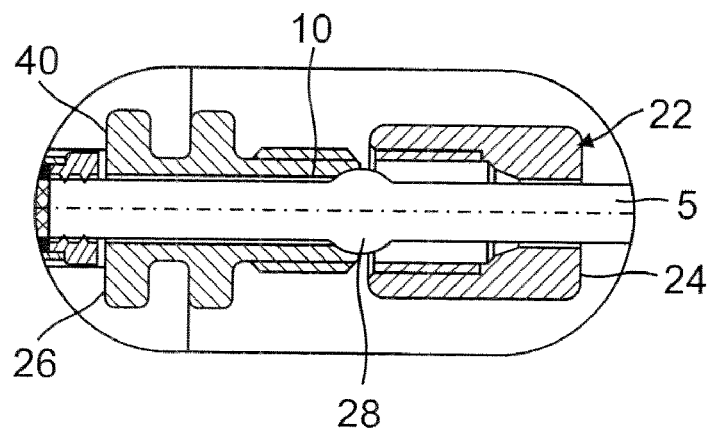
FIG. 6 is an alternative embodiment provided in accordance with aspects of the present invention.

FIG. 6 is a cross-sectional side view of an alternative locking device 22 provided in accordance with aspects of the present invention. The locking the device 22 is similar to the device described with reference to FIGS. 1-5 with the exception of an enlarged portion for compressing by a threaded nut 24 and a threaded sleeve 26. In the present embodiment, a bead 28 is used as an enlarged portion to be compressed by the sleeve and the nut. When the threaded nut 24 fully engages the threaded cylindrical projection 10, the bead is compressed in the cavity defined by the nut and the sleeve to form a fluid tight seal against the interior surface of the cavity. In one embodiment, the bead 28 is singularly molded with the lead cable 5 and is fixed relative to the medical lead. Alternatively or in addition thereto, the bead could be bonded or glued to the lead.

Although limited preferred embodiments and methods for making and using a locking device provided in accordance with aspects of the present invention have been specifically described and illustrated, many modifications and variations will be apparent to those skilled in the art. For example, the sleeve may be from a difference material, may include a third or other flanges, and may include two similar sleeves located side-by-side for connecting to two connector stacks, also located side-by-side, etc. Moreover, the locking device provided herein may be used in conjunction with an Extension, which is used for testing implanted electrode terminals or implanted activator units so that programs or controls used to manipulate the implanted electrode terminals and the like can be programmed for the IMD. Still alternatively, the connector assembly and the locking device may be used for any device that requires an in-line connection in which multiple conductive sources are to be relayed between a source generator and a source receiver, whether that device is configured for implanting or otherwise. For example, the in-line connector having a locking assembly as provided in accordance with aspects of the present invention may be used in automotive applications, aerospace applications, oil and gas applications, consumer electronics applications, etc. to transfer one or multiple signals in parallel or in series. Accordingly, it is to be understood that the connector assembly and locking device constructed according to principles of this invention may be embodied in other than as specifically described herein. The invention is also defined in the following claims.

What is claimed is:

1. A locking mechanism for a connector comprising:
a sleeve located on a housing having first threaded member extending externally of the housing and having an opening to a cavity at an end of the externally extending first threaded member, said cavity tapering inwardly from said opening to form an entrance to a bore;
a lead sized for insertion into the opening and the bore of the sleeve, the lead having a nominal outside diameter section and including an enlarged section with an outer diameter greater than the nominal outside diameter section of the lead;
a second threaded member for surrounding the enlarged section, the second threaded member being moveable along the axis of the lead; and
at least two conductive rings each comprising a bore spaced apart from one another by a non-conductive spacer located in-line with the sleeve such that the bore of the sleeve is co-axial with the bore of each of the at least two conductive rings:
wherein the second threaded member is threadedly engaged to the first threaded member to secure, at least in part, the enlarged section within the cavity of the sleeve and to secure the lead, at least in part, within the bore of the sleeve; and wherein the enlarged section comprises two tapered ends.

2. The locking mechanism of claim 1, wherein the enlarged section is a ferrule that is axially movable on the lead prior to the second threaded member being threadedly engaged to the first threaded member and wherein the lead comprises conductive elements and non-conductive elements spaced along at least a section of the lead.

3. The locking mechanism of claim 1, wherein the enlarged section is a bead fixedly formed upon the lead.

4. The locking mechanism of claim 1, wherein the housing is a header located in an implantable medical device.

5. The locking mechanism of claim 1, wherein the sleeve comprises two spaced apart flanges defining a mold space therebetween.

6. The locking mechanism of claim 1, wherein the second threaded member is a nut having a bore having the lead projecting therethrough.

7. The locking mechanism of claim 1, wherein the sleeve is attached to the housing by molding.

8. The locking mechanism of claim 1, wherein the at least two conductive rings are connected to electrodes.

9. The locking mechanism of claim 4, wherein the implantable medical device is a pulse generator.

10. An in-line connector comprising an in-line stack having a common bore positioned in a housing, which is attached to source generator or a source receiver;
a locking device comprising a portion covered by the housing and a portion extending away from the housing; said locking device further comprising a threaded nut and a sleeve comprising a bore aligned to the common bore of the in-line stack and having a removable ferrule received in a bore holding section of the sleeve; and
at least two conductive rings each comprising a bore spaced apart from one another by a non-conductive spacer located in-line with the sleeve such that the bore of the sleeve is aligned with the bore of each of the at least two conductive rings;
wherein the ferrule is configured to compress inside the bore holding section when the threaded nut is threaded to the sleeve.

11. The in-line connector of claim 10, wherein the ferrule comprises a body having a bore and two open ends.

12. The in-line connector of claim 11, wherein the bore comprises an enlarged cavity.

13. The in-line connector of claim 10, wherein the housing is part of a header of an implantable medical device.

14. The in-line connector of claim 10, wherein the sleeve comprises two spaced apart flanges defining a mold cavity therebetween.

15. A method for locking a lead to an in-line stack comprising: inserting the lead into a common bore of the in-line stack and a bore of a sleeve comprising an elongated section comprising exterior threads, positioning a ferrule in mechanical communication with the sleeve and the lead, and turning a nut comprising interior threads to engage the exterior threads of the elongated section: and wherein the in-line stack comprises at least two spaced apart conductive rings having a common bore.

16. The method of claim 15, further comprising connecting a plurality of electrodes located inside the lead to at least one of a source generator and a source receiver.

* * * * *